Figure 2:
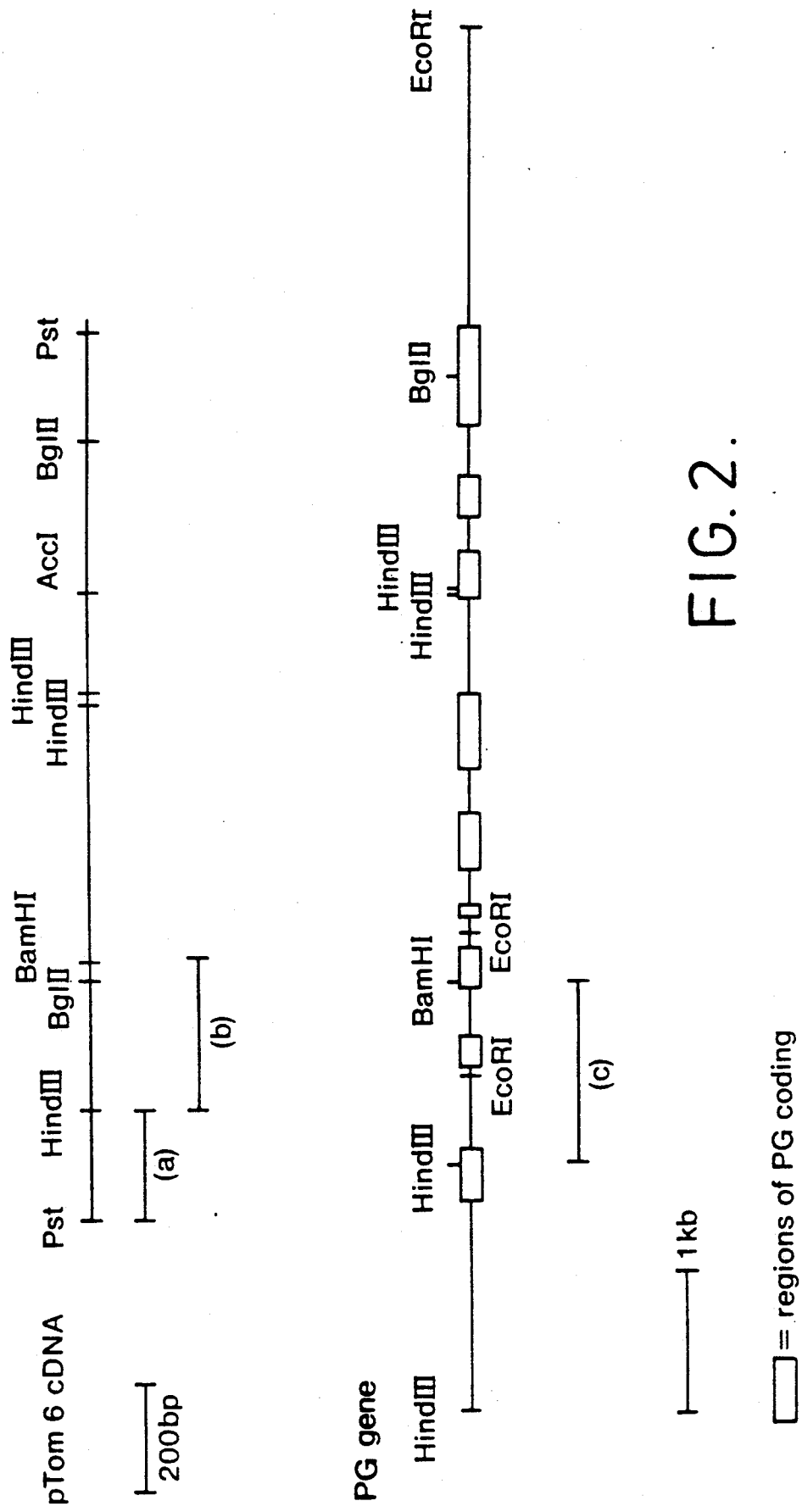

United States Patent [19]

Bridges et al.

[11] Patent Number: 5,073,676
[45] Date of Patent: Dec. 17, 1991

[54] TOMATO ANTI-SENSE PECTIN ESTERASE

[75] Inventors: Ian G. Bridges, Cheshire; Wolfgang W. Schuch, Frodshan; Donald Grierson, Shepshed, all of England

[73] Assignee: Imperial Chemical Industries PLC, London, England

[21] Appl. No.: 419,779

[22] Filed: Sep. 29, 1989

Related U.S. Application Data

[63] Continuation of Ser. No. 119,614, Nov. 12, 1987.

[30] Foreign Application Priority Data

Nov. 11, 1986 [GB] United Kingdom ................. 8626879

[51] Int. Cl.$^5$ ........................ C12N 15/29; A01H 5/00
[52] U.S. Cl. ................................. 800/205; 435/172.3; 435/320.1; 435/240.4; 800/DIG. 44; 935/35; 935/67
[58] Field of Search ..................... 435/172.3, 317.1, 68, 435/240.4, 320.1; 935/64, 67, 35; 536/27; 800/205, DIG. 44

[56] References Cited

U.S. PATENT DOCUMENTS 4,801,540 1/1989 Hiatt et al. ........................ 435/172.3

OTHER PUBLICATIONS

Woods (1984), Focus 6(3): 1-2.
Beran (1984), Nucleic Acids Research, 12: 8711-8721.
Ecker et al. (1986), Proceedings National Academy of Science, 83: 5372-5376.
Markoviz et al. (1986), Eur. J. Biochem., 158: 455-462.
Kotoujansky et al. (1985), The EMBO Journal, 4: 781-785.
DellaPenna et al. (Sep. 1986), Proceedings National Academy of Science, 83: 6420-6424.
Horsch et al. (Mar. 1985), Science, 227: 1229-1231.
Giovannoni et al. (Jan. 1989), The Plant Cell, 1: 53-63.
Slater et al. (1985), Plant Molecular Biology, 5: 137-147.

*Primary Examiner*—Elizabeth C. Weimar
*Assistant Examiner*—Che S. Chereskin
*Attorney, Agent, or Firm*—Cushman, Darby & Cushman

[57] ABSTRACT

Recombinant DNA comprises promoter and terminator base sequences respectively upstream and downstream of an inverted base sequence complementary to a substantial sequence of bases in polygalacturonase mRNA. The antisense mRNA produced thereby delays softening of fruit, in particular tomatoes.

9 Claims, 5 Drawing Sheets

FIG. 1.

DNA sequence of pTom 6

```
                            M  V  I  Q  R  N  S  I  L  L  I  I  F  A  S  S  I  S  T  C  R  S
AATCTTTTCAATAGACAAGTTAAAAACCATATACCATATAACAATATCATGGTTATCATGGAATAGTATTCCTTCTCATTATTATTTTTGCTTCATCAATTTCAACTTGTAGAA     120
        10         20        30        40        50        60        70        80        90        100       110      120

N  V  I  D  D  N  L  F  K  Q  V  Y  D  N  I  L  E  Q  E  F  A  H  D  F  Q  A  Y  L  S  Y  L  S  K  N  I  E  S  N  N
GCAATGTTATTGATGACAATTTATTCAAAGCAAGTTTATGATAATATTCTTGAACAAGAATTTGCTCATGATTTTCAAGCTTATCTTTCTTATTTGAGCAAAAATATTGAAAGCAACAATA    240
    130       140       150       160       170       180       190       200       210       220       230       240

I  D  K  V  D  K  N  G  I  K  V  I  N  V  L  S  F  G  A  K  G  D  G  K  T  Y  D  N  I  A  F  E  Q  A  H  N  E  A  C  S
ATATTGACAAGGTTGATAAAAATGGGATTAAAGTAATAAATGTACTTAGCTTTGGAGCTAAGGGTGATGGAAAAACATATGATAATATTGCATTTGAACAAGCATGAATGAAGCATGTT    360
        250       260       270       280       290       300       310       320       330       340       350       360

S  R  T  P  V  Q  F  V  V  P  K  N  K  N  Y  L  L  K  Q  I  T  F  S  G  P  C  R  S  S  I  S  V  K  I  F  G  S  L  E  A
CATCTAGAACACCTGTTCAATTTGTTGTTCCTAAAAACAAGAATTATCTTCTCAAGCAAATCACCTTTTCAGGTCCATGCAGATCTTCTATTTCAGTAAAGATTTTTGGATCCTTAGAAG    480
    370       380       390       400       410       420       430       440       450       460       470       480

S  S  K  I  S  D  Y  K  D  R  R  L  H  I  A  F  D  S  V  Q  N  L  V  V  G  G  G  G  T  I  N  G  N  G  Q  V  H  N  P  S
CATCTAGTAAAATTTCAGACTACAAAGATAGAAGGCTTTGATTGCTTTGATAGTGTTCAAAATTTAGTTGTTGGAGGAGGAGGAACTATCAATGGCAATGGACAAGTATGGTGGCCAA    600
        490       500       510       520       530       540       550       560       570       580       590       600

S  C  K  I  N  K  S  L  P  C  R  D  A  P  T  A  L  T  F  W  N  C  K  N  L  K  V  N  N  L  K  S  K  N  A  Q  Q  I  H  I
GTCTTGCAAAATAAAATCACTTGCCATGCAGGATGCAGGAGGATCACCAACGGCCTAACCTTCTGGAATTGCAAAAATTTGAAAGTGAATAATCTAAAGAGTAAAAATGCACAACAAATTCATA    720
    610       620       630       640       650       660       670       680       690       700       710       720

K  F  F  S  C  T  N  V  V  A  S  N  L  M  I  N  A  S  K  S  P  N  T  D  G  V  H  V  S  N  T  Q  Y  I  Q  I  S  D  T
TCAAATTTGAGTCATGGACTAATGTTGTAGCTTCTCAAATGCTTCAGGCAAAGAGCCCAAATACTGATGGAGTCCATGTATCCAATACTCAATATATTCAAATATCTGATA    840
        730       740       750       760       770       780       790       800       810       820       830       840
```

FIG. 1. (CONT'D)

DNA sequence of pTom 6

```
  I  I  G  T  G  D  D  C  I  S  I  V  S  G  S  Q  N  V  Q  A  T  N  I  T  C  G  P  G  H  G  I  S  I  G  S  L  G  S  G  N
CTATTATTGGAACAGGTGATGATTGTATTTCAATTGTTTCTGGATCTCAAAATGTGCAGGCCACAAATATTACTTGTGTCCAGGTCATGGTATAAGTATTGGAAGCTTAGGATCTGGAA
     850       860       870       880       890       900       910       920       930       940       950       960
  S  E  A  Y  V  S  N  V  T  V  N  E  A  K  I  I  G  A  E  N  G  V  R  I  K  T  H  Q  G  G  S  G  Q  A  S  N  I  K  F  L
ATTCAGAAGCTTATGTGTCTAATGTTACTGTTAATGAAGCCAAAATTATTGGTGCCGAAAATGGAGTTAGGATCAAGACTCATCAAGGAGGATCTGGACAAGCTAGCAACATCAAATTC
     970       980       990      1000      1010      1020      1030      1040      1050      1060      1070      1080
  N  V  E  H  Q  D  V  K  Y  P  I  I  D  Q  N  Y  C  D  R  V  E  P  C  I  Q  Q  F  S  A  V  Q  V  K  N  V  V  Y  E  N
TGAATGTGGAAATGCAAGACGTTAAGTATCCATTATAGACCAAAACTATTGTGATCGAGTTGAACCATGTATACAACAGTTTCAGCAGTTCAAGTGAAAAATGTGGTGTATGAGA
    1090      1100      1110      1120      1130      1140      1150      1160      1170      1180      1190      1200
  I  K  G  T  S  A  T  K  V  A  I  K  F  D  C  S  T  N  F  P  C  E  G  I  I  M  E  N  I  N  L  V  G  E  S  G  K  P  S  E
ATATCAAGGGCACAAGTGCAACAAAGGTGCCATAAAATTTGATTGCAGCACAAACTTTCCATGTGAAGGAATTATAATGGAGAATATAAATTTAGTAGGGGAAAGTGGAAAACCATCAG
    1210      1220      1230      1240      1250      1260      1270      1280      1290      1300      1310      1320
  A  T  C  K  N  V  H  F  N  N  A  E  H  V  T  P  H  C  T  S  L  E  I  S  E  D  E  A  L  L  Y  N  Y  *
AGGCTACGTGCAAAAATGTCCATTTTAACAATGCTGAACATGTTACACCACACTGCACTTCACTGAAGATGAAGCTCTTTTGTATAATTATATGTATTTCTATTTCTA
    1330      1340      1350      1360      1370      1380      1390      1400      1410      1420      1430      1440

TCAATATATAGCAGATATGATATATCACAATAAACAAATCTATATCTATGTATTGAATAATTATTATATGTACGGATTGAAGTTTAATAAGACTACTATGTATTTCTATTTCTA
    1450      1460      1470      1480      1490      1500      1510      1520      1530      1540      1550      1560

GTCAAAAGTTTGACGATTGTACTTTTTAATGTACAAAAATAATAAAAATGGTTATTTATATGAAAAAAAAAAAAAAA
    1570      1580      1590      1600      1610      1620      1630
```

FIG. 3.

DNA sequence of pPE1

```
CTTAACTGATTGTCTTGAGCTTCTTGATCTGTCAGTTGATTCAATTGATAAGAAGAAGTCGTTCGGAGCATGCCAATGCCAAAAGTTGGCTAAGTGGTG
        10        20        30        40        50        60        70        80        90       100       110       120
                                                                 M  I  N  G  T  N  L  D  E  L  I  S  R  A  K  V  A  L  A  M  L  A  S

TGCTTACTAACCACGTTACGTGCTTGGATGAGCTTGATTCCTTTACTAAAGCTATAAAGCTAAGGTAGCATTGGCGATGCTTGCGT
       130       140       150       160       170       180       190       200       210       220       230       240
 V  T  T  P  N  D  E  V  L  R  P  G  L  G  K  H  P  S  H  V  S  S  R  D  R  K  L  M  E  S  S  G  K  D  I  G  A  N  A  V

CTGTGACAACTCCAAATGATGAAGTTTTGAGGCCTGGGTTTAGGAAAACATGCCATCTTCGAGGATAGGAGAAGCTGATGGAGAGTTCGGGTAAGGACATTGGAGCGAATGCAG
       250       260       270       280       290       300       310       320       330       340       350       360
 V  A  K  D  G  T  G  K  Y  R  T  L  A  E  A  V  A  A  A  P  D  K  S  K  T  R  Y  V  I  Y  V  K  R  G  T  Y  K  E  N  V

TGGTGGCAAAAGATGGAACAGGGAAATATCGAACACTTGCTGAAGCTGTTGCTGCAGCACCAGATAAGAGTAAGACGCGTTATGTATTTATGTAAAGAGGGAACTTATAAAGAGAATG
       370       380       390       400       410       420       430       440       450       460       470       480
 E  V  S  S  R  K  H  N  L  H  I  I  G  D  G  H  Y  A  T  I  I  T  G  S  L  N  V  V  D  G  S  T  T  F  H  S  A  T  L  A

TTGAGGTGAGTAGCAGGAAAATGAATTGATTGGTGATGGCATGTATGCTACCATCATCACTGGGAGCCTTAATGTGTCGATGGATCAACAACCTTCCACTCTTGCCACTCTTG
       490       500       510       520       530       540       550       560       570       580       590       600
 A  V  G  K  G  F  I  L  Q  D  I  C  I  Q  N  T  A  G  P  A  K  H  Q  A  V  A  L  R  V  G  A  D  K  S  V  I  N  R  C  R

CTGCCAGTTGGCAAAGGATTCAAGAACACCCTTATACTACTAGGGAACAAGGACTAAACACCAAGCTGTTGCACTTCGAGTTGGAGCTGGAGAGCTGATAAGTCTGTCATAAATCGTTGTC
       610       620       630       640       650       660       670       680       690       700       710       720
 I  D  A  Y  Q  D  T  L  Y  A  H  S  Q  R  Q  F  Y  Q  S  S  Y  V  T  G  T  I  D  F  I  F  G  N  A  A  V  F  Q  K  C

GTATGCGATGCTTATCAAGAGACACCCTTATGCACATTCTCAAAGGACAAATTCTATCAGAGACTCGTAACAGGACTATTGATTCATATTCGGTAATGCAGTTGTATTCCAGAAAT
       730       740       750       760       770       780       790       800       810       820       830       840
```

FIG. 3.(CONT'D)

DNA sequence of pPE1

```
  Q  L  V  A  R  K  P  G  K  Y  Q  Q  N  M  V  I  A  Q  G  R  T  D  P  N  Q  A  T  G  T  S  I  Q  F  C  D  I  I  A  S  P
GCCAGCTCGTAGAGAAACCGGGTAAATACCAGCAAAACATGGTGATCGCACAAGGACGGAGGACGAGACCCAAATCAGGGCCACGGGGACATCAATTCAGTTTTGTGATATAATAGCAAGTC
    850       860       870       880       890       900       910       920       930       940       950       960
  D  L  K  P  V  V  K  E  F  P  T  Y  L  G  R  P  H  K  K  Y  S  R  T  V  V  H  E  S  S  L  G  G  L  I  D  P  S  G  H  A
CTGACCTAAAACCAGTCGTGAAAGAATTCCCAACATATCTTGGTAGGCCATGGCCATAAGAACTGTAGTGATGGAATCATCATTGGGTGGTCTCATTGATCCATCCGGGTTGGG
    970       980       990      1000      1010      1020      1030      1040      1050      1060      1070      1080
  E  H  H  G  D  F  A  L  K  T  L  Y  Y  G  E  F  M  N  N  G  P  G  A  G  T  S  K  R  V  K  N  P  G  Y  H  V  I  T  D  P
CTGAGTGGCACGGGAGATTTTGCGTAAAGACATTGTGTTATGGTGAATTTATGAATAATGGACCTGGTGCTGGTACTAGTAAGCGTGTCAAGTGGCCTATGCATGTCATTACTGACC
   1090      1100      1110      1120      1130      1140      1150      1160      1170      1180      1190      1200
  A  E  A  M  S  F  T  V  A  K  L  I  Q  G  S  H  L  R  S  T  D  V  A  Y  V  D  G  L  Y  D  Y  S  D  I  K  L  L  F  V
CCGCTGAAGCTATGTCACTGTGCTAAGCTGATTCAGGGCCGGATCATGTTGAGGTCTACTGACGTCTACGTGGCGTGTATGTGGATGGATTATATGATTATATGTGATATAAAATACTCTTTG
   1210      1220      1230      1240      1250      1260      1270      1280      1290      1300      1310      1320
  Y  V  T  R  H  L  *
TTTATGTAACAAGACATCTTAAAAGTTCAAAGTAAGTAGTAATATATCCATATGAAGTGCCACATGAGCGCAGAGCGGATTAAAGCATAAACACAACTCTAGT
   1330      1340      1350      1360      1370      1380      1390      1400      1410      1420      1430      1440
GTGACAAGCATTTACATGGCTCATTCCTTACTACTAAGTCGTCAATAAGTTCAGTTAAGGGGTTCATAAGGTTAAGTTAATACTAAGTGTATATAATATATTTATGGCCGATAAAGCTGAACTGATGATG
   1450      1460      1470      1480      1490      1500      1510      1520      1530      1540      1550      1560
CTTTAATGTAATTATAGTTTTCTGAAAAAGGATATGTGTAATATTAGGTTTTTCCCTGATGTTTATGGTTGTGGGGTGGTTGGTTATGATAAAAATATATGATAAAGATGAAAAAAAAAAAA
   1570      1580      1590      1600      1610      1620      1630      1640      1650      1660      1670      1680
```

TOMATO ANTI-SENSE PECTIN ESTERASE

This is a continuation of application Ser. No. 119,614, filed Nov. 12, 1987.

This invention relates to DNA, and to vectors and plant cells containing such DNA, and to plants composed of such cells. In one aspect, the invention relates to flowering and fruiting plants, for example tomatoes, and to such plants having usefully altered ripening properties.

It has been shown that tomato ripening is a process involving the activation of specific genes (D. Grierson, 1985, CRC Critical Reviews in Plant Sciences 3, 113-132). The features of many of these genes have not been defined. However, one such gene has been shown to produce polygalacturonase (PG), the enzyme primarily responsible for degrading the cell wall. The synthesis of PG begins in tomatoes during early stages of ripening, and reaches a maximum at the soft red stage. This increase is paralleled closely by an increase in PG mRNA (Grierson et al, 1985, Planta 163, pp. 263-271).

Various investigations, including enzyme analysis, indicate that the PG gene, in tomatoes, is only expressed in ripening fruit (Maunders et al, 1986, in press) and in flower abcission zones.

A hitherto unpublished paper of which the present inventors are authors (Grierson et al, 1986, Nucleic Acid Reviews, 14 p 8595-8603) describes the preparation of cDNA from PG mRNA, and discloses in particular pTOM6, a plasmid containing substantially all (all but the first 20 bases) of the cDNA sequence complementary to the mRNA that is generated in the ripening tomato and that is translated into PG.

We now propose to regulate the expression of the PG gene in flowering and fruiting plants (such as tomatoes) by generating antisense RNA to PG sequences in such fruit. Such RNA hinders the expression of the PG mRNA, probably by forming therewith a double-stranded complex.

I had previously been proposed to regulate gene expression in both prokaryotes and eukaryotes by generating antisense RNA therein; and such proposals have included higher plants (Ecker et al, 1986, PNAS 83, pp. 5372-5376). However, we are aware of no prior proposals for using antisense RNA corresponding to a natural plant gene to control plant biochemistry or development.

According to the present invention we provide recombinant DNA comprising an upstream promoter base sequence, a base sequence for transcription into mRNA under control of said upstream promoter base sequence, and a downstream transcription terminator base sequence, characterized in that the base sequence for transcription comprises an inverted sequence of bases complementary to a substantial run of bases in mRNAs encoding fruit softening enzymes.

Examples of fruit softening enzymes are polygalacturonase and pectin methylesterase.

We further provide vectors containing such DNA; method of making such vectors by cloning of the desired base sequence for transcription in the appropriate orientation into an existing vector containing the desired promoter and terminator base sequences; plant cells containing such DNA, as well as plants (in particular tomatoes) constituted of such plant cells.

DNA according to the invention preferably comprises a base sequence for transcription at least 50 bases in length. There is no theoretical upper limit to the base sequence—it may be as long as the relevant mRNA produced by the cell—but for convenience it will generally be found suitable to use sequences between 100 and 1000 bases in length.

The invention will be further described with reference to the drawings, in which:

FIG. 1 gives the base sequence for the polygalacturonase cDNA clone pTOM6;

FIG. 2 shows schematically the fragments of pTOM6 and of following Examples and Experiments;

FIG. 3 gives the base sequence for the pectin esterase clone pPE1.

A very convenient source of DNA for use as the base sequence for transcription is provided by DNA that gives rise to polygalacturonase mRNA.

The required antisense DNA can be obtained by cutting with restriction enzymes an appropriate sequence of such (mRNA-polygalacturonase producing) DNA; and then cloning the cut DNA into a vector containing upstream promoter and downstream terminator sequences, the cloning being so carried out that the cut DNA sequence is inverted with respect to its orientation in the strand from which it was cut.

In the new vector, the strand that was formerly the template strand becomes the coding strand, and vice versa. The new vector will thus produce RNA in a base sequence which is complementary to the sequence of polygalacturonase mRNA. Thus, the two RNA strands are complementary not only in their base sequence but also in their orientations (5' to 3').

As source of the polygalacturonase DNA base sequence for transcription, it is convenient to use a cDNA clone such as pTOM6. The base sequence of pTOM6 is set out in FIG. 1. A cDNA clone such as pTOM6 may be obtained from the mRNA of ripening tomatoes by the method described by Slater at al, Plant Molecular Biology 5, 137-147. In this way may be obtained sequences coding for the whole, or substantially the whole, of the mRNA that is translated into PG. Suitable lengths of the cDNA so obtained may be cut out for use by means of restriction enzymes.

An alternative source of DNA for the base sequence for transcription is the PG gene. It differs from that in the cDNA of, eg. pTOM6, in that introns are present. The introns are not transcribed into mRNA (or, if so transcribed, are subsequently cut out). The major part of the PG gene has been deposited as gTOM23 with the National Collections of Industrial and Marine Bacteria, Aberdeen, under Accession No. 12373. When using the PG gene as the source of the base sequence for transcription it is preferred to use primarily exon regions.

A further way of obtaining a suitable DNA base sequence for transcription is to synthesize it ab initio from the appropriate bases, for example using FIG. 1 as a guide.

Recombinant DNA and vectors according to the present invention may be made as follows. A suitable vector containing the desired base sequence for transcription (for example PTOM6) is treated with a restriction enzyme to cut the sequence out. The DNA strand so obtained is cloned (in reverse orientation) into a second vector containing the desired promoter sequence (for example CAMV 35S or the PG gene promoter sequence) and the desired terminator sequence (for example the 3' end of the nopaline synthase gene, the nos 3' end).

It is often preferred, in applying the invention, to use the promoter of the PG gene. Use of this promoter, at least in tomatoes, has the advantage that the production of antisense RNA is under the control of the same system that controls PG mRNA. Thus whatever factors tend to produce the latter will tend at the same time to produce the former to interfere with it.

Vectors according to the invention may be used to transform plants as desired, to make plants according to the invention. Dicotyledenous plants, such as the tomato, may be transformed by Ti plasmid technology, for example as described by Bevan (1984) Nucleic Acids Research, 12, 8711-721.

Such transformed plants may be reproduced sexually, or by cell culture.

The degree of production of antisense RNA in the plant cells can be controlled by suitable choice of promoter sequences, or by selecting the number of copies, or the site of integration, of the DNA sequences according to the invention that are introduced into the plant genome. In this way, for example, it may prove possible to delay softening of tomatoes for a greater or lesser period after ripening.

The following Examples and Experiments illustrate the invention and how to carry it out. Examples relate to the manufacture of vectors according to the invention: Experiments relate to preparation of starting materials. All cloning procedures are performed under standard conditions as described by Maniatis et al (1982) "Molecular Cloning", Cold Spring Harbor Laboratory. Vectors for which an NCIB Accession number are given have been deposited at the National Collections of Industrial and Marine Bacteria, Torry Research Station, PO Box 31, 135 Abbey Road, Aberdeen AB9 8DG, Scotland.

EXPERIMENT 1

Construction of the plasmid pPH1

A. Isolation of the nos 3' end.

10 μg of pWRECK2-CAMV-CAT-1 (NCIB Accession No. 12352) is digested with PvuI in order to linearize the DNA, under conditions recommended by the manufacturer. The completeness of digestion is analyzed by running an aliquot of the reaction of 0.8% agarose gels. The reaction is stopped by extraction with phenol/chloroform. DNA is precipitated with ethanol and dried under vacuum. The cohesive ends are removed by incubation of the linearized DNA with T4 polymerase at 37° C. for 30 minutes. The enzyme is inactivated by incubation at 65° C. for 15 minutes. The reaction volume is increased by the addition of HindIII buffer and HindIII enzyme is added. The reaction is carried out for 2 hours at 37° C. The 250 bp PvuI/HindIII fragment is isolated from agarose gels by electroelution. DNA is phenol/chloroform extracted, precipitated with ethanol and resuspended in water.

B. Linearization of pUC18. 2 μg of pUC18 (plasmid commercially available eg. from Amersham) DNA is digested with SphI under conditions recommended by the manufacturer. The reaction is stopped by extraction with phenol/chloroform. Cohesive ends are removed by treatment with T4 polymerase for 30 minutes at 37° C. The buffer volume is increased, and HindIII is added. The mixture is incubated for 2 hours at 37° C. The reaction is stopped by extraction with phenol/chloroform. DNA is precipitated with ethanol and resuspended in water at 100 ng/ml.

C. Cloning of nos. 3' end into pUC18 to give pNOS1.

1 μl of pUC18 prepared under (B) is ligated with 100 ng of nos 3' end prepared under (A) in a total of 15 μl in the presence of T4 ligase. Incubation is carried out for 24 hours at 16° C. An aliquot of the ligation is transformed into competent TG2 cells. An aliquot of the transformation mix is plated onto ampicillin and Xgal containing plates. White colonies are picked, and the DNA examined by restriction analysis. Molecules containing the nos 3' end are characterized by the presence of a 260 base pair HindIII/BamHl fragment. These plasmids are called PNOS1.

D. Preparation of the CaMV 35S promoter

The CaMV promoter is obtained by digestion of pWRECK2-CAMV-CAT-1 (NCIB Accession No. 12352) with ScaI for 2 hours at 37° C. An aliquot of the restriction digest is analyzed by electrophoresis on agarose gels. The reaction is stopped by extraction with phenol/chloroform. After ethanol precipitation and resuspension in water, the DNA is cut with HphI for 2 hours at 37° C. The cohesive ends are removed by treatment with T4 polymerase under standard conditions. The CaMV promoter 629 base pair fragment is isolated by agarose gel electrophoresis and subsequent electroelution.

E. Linearization of pNOS1 2 μg of pNOS1 is cut with SstI at 37° C. for 2 hours. After completion of the reaction, T4 polymerase is added in order to remove the cohesive ends. The reaction is stopped by extraction with phenol/chloroform. Then DNA is precipitated with ethanol and resuspended in water at 100 ng/μl.

F. Cloning of CaMV 35S promoter into pNOS1

PNOS1 Prepared as under (E) is ligated to CaMV35S promoter fragment prepared under (D) under standard conditions using T4 ligase. The reaction is carried out for 24 hours at 16° C. An aliquot of the ligation mixture is transformed into competent TG2 cells, and Plated onto ampicillin containing Xgal plates. DNA is isolated from transformants and analyzed by restriction with NcoI and HindIII. Molecules containing the CaMV 35S promoter in the correct orientation are characterized by the presence of a 920 base pair fragment. These plasmids are called pPH1.

EXPERIMENT 2 : Preparation of Plasmid pCB1

A. Isolation of a PG promoter fragment

Genomic clones are isolated from a partial Sau3A library of Ailsa Craig tomato DNA cloned into EMBL3 (Bird et al, in preparation). PG clones are isolated from the genomic library by screening with both the complete PTOM6 cDNA insert, and the isolated 5' PstI/HindIII fragment from PTOM6 (Grierson et al, NAR 1986). Several overlapping clones are isolated and the transcription start site of the PG gene located by S1 mapping experiments (Bird et al in preparation 1987). The pG promoter can be located on a 1.6 Kb HindIII fragment which also contains part of the PG coding information.

B. Insertion of a SpeI site into the PG promoter

In order to be able to manipulate the PG promoter sequence conveniently (ie. the DNA 5' to the transcription start) a SpeI site is introduced by site directed mutagenesis using standard protocols. The HindIII fragment is isolated from genomic clone gTOM23 (NCIB Accession No. 12373), and cloned into the HindIII site of (commercially available vector) M13 mp19. After annealing with a suitable mismatch primer and extension using DNA polymerase, the mixture is transformed into competent TG2 cells. Phages are plated and duplicated filters were prepared for hybridization to the labelled mismatch primer. Putative clones are identified by hybridization under increasingly stringent conditions, isolated and the generation of the Spel site is determined by direct DNA sequence anaiysis. The promoter fragment is isolated from one isolate by restriction with Spel and HindIII. This fragment is then cloned into pUC19 (commercially available plasmid) cut with HindIII and XbaI. The promoter fragment is then transferred into Bin19 (Bevan, Nucleic Acid Research, 1984, 12, 8711-8721) cut with BamHI and HindIII. This plasmid is called pCB1.

EXPERIMENT 3: Preparation of Plasmid pPH2

A. Isolation of the PG promoter fragment from pCB1

5 μg of pCBl (prepared as in Experiment 2) is cut with HindIII for 2 hours at 37° C. The mixture is phenol/chloroform extracted and DNA precipitated with ethanol. After re-suspension in water the cohesive ends are filled in using DNA polymerase under standard conditions at room temperature for 15 minutes. The polymerase is inactivated by heating to 65° C. for 15 minutes. The DNA is then treated with BamHl for 2 hours at 37° C. The PG promoter fragment is then by electroelution isolated by agarose gel electrophoresis as a HindIII/BamHl 1.45 Kb fragment.

B. Preparation of pPHl for insertion of the PG promoter fragment

5 μg of pPHI (prepared as in Experiment 1) is cut with Ncol for 2 hours at 37° C. under standard conditions. The DNA is purified by phenol/chloroform extraction. The cohesive ends are filled in using DNA polymerase I Klenov fragment for 15 minutes at room temperature. The volume is increased and BamHI added. The mixture is incubated for 2 hours at 37° C. The mixture is then separated on agarose gels, and the large fragment of approximately 3 Kb isolated by electroelution.

C. Cloning of the PG promoter into the large fragment from pPH1.

10 μg of pPHl prepared as in Experiment 1 is ligated with the PG promoter fragment as prepared in A under standard conditions for 24 hours at 16° C. An aliquot of the ligation mixture is used to transform competent TG2 cells. Aliquots of the transformation mixture are plated onto L plates containing ampicillin and Xgal. Colonies are picked and examined for the presence of the PG promoter DNA by electrophoresis to detect an increase in the size of the vector and by direct DNA sequence determination. This plasmid is called pPH2.

EXAMPLE 1: Preparation of Plasmids pJR10 and pJR11

A. Preparation of the antisense DNA

A 730 base pair Hinfl fragment covering the 5' untranslated region, the putative leader sequence, and a substantial portion of the PG coding region is isolated from pTOM6. 5 μg pTOM6 is restricted with Hinfl for 2 hours at 37° C. The reaction is stopped by extraction with phenol/chloroform, and ethanol precipitated. Cohesive ends are removed by treatment with T4 polymerase under standard conditions. DNA is purified by phenol/chloroform extraction and ethanol precipitation.

B. Cloning of the antisense DNA into pPHl

The DNA fragment as isolated in Example 1.A is cloned into the SmaI site of pPHl. pPH1 DNA is restricted with SmaI under standard conditions for 2 hours at 37° C. After incubation for 2 hours bacterial alkaline phosphatase is added in order to prevent self-ligation of pPHl during subsequent cloning steps. The reaction is stopped by extraction with phenol/chloroform. DNA is precipitated and resuspended in water. An aliquot of the DNA as prepared in (A) is ligated under standard conditions to SmaI cut pPHl. Aliquots of the ligation mixture are transformed into competent TG2 cells, and plated onto ampicillin containing plates. Recombinants are analyzed by restriction digestion with HindIII. Both antisense (pPH10) and "sense" (pPH11) constructs are isolated.

EXAMPLE 2: Preparation of Plasmids pPH20 and pPH21

A. Cloning of the antisense DNA into pPH2

DNA as isolated in Example 1A is cloned into pPH2 cut with HincII. The plasmid containing the PG sequence in the antisense orientation is called pPH20, the plasmid containing the PG DNA in the sense orientation is called pPH21.

EXAMPLE 3: Transformation of Tomato Plants

Transformation of tomato plants is achieved using a modification of the leaf disc transformation protocol published by Bevan et al, EMBO Journal 4, 1921-1926, 1985. Transformed tomato plants are analyzed for the presence of the antisense constructs by Southern hybridization to genomic DNA. Expression of sense and antisense RNA is monitored by dot blot and Northern hybridizations. Firmness of the fruit is investigated using general physiological methods. The presence of antisense PG constructs in the cells of the ripening tomatoes is associated with firmness in the tomato being maintained for a longer period.

There follows a second series of Examples and Experiments which have been carried out according to the same general scheme.

EXPERIMENT 11

Construction of the plasmid pJR1

A. Isolation of the nos. 3' end

This was carried out according to the method of Experiment 1 above.

B. Removal of the CaMV 3' end from pDH51

2 μg of pDH51 (Pietrzak et al, (1986) Nucleic Acids Research 14, 5857-5868) was digested with SphI at 37° C. for hours under standard conditions. The reaction was stopped by extraction with phenol/chloroform. DNA was precipitated with ethanol and resuspended in water. Cohesive ends were removed by treatment with T4 polymerase for 30 minutes at 37° C. The buffer volume was increased, and HindIII was added. The mixture was incubated for 2 hours at 37° C. The resulting 3.2 Kb fragment was isolated after gel electrophoresis on agarose gels by electroelution. The DNA was extracted with phenol and chloroform, precipitated with ethanol and resuspended in water.

C. Cloning of nos 3' end into pDH51 to give pJR1

1 μl of pDH51 prepared under (B) was ligated with 100 ng of nos 3' end prepared under (A) in a total of 15 μl in the presence of T4 ligase. Incubation was carried out for 24 hours in 16° C. An aliquot of the ligation was transformed into competent TG2 cells. An aliquot of the transformation mix was plated onto ampicillin and Xgal containing L- plates. White colonies were picked, and the DNA examined by restriction analysis. Molecules containing the nos 3' end were characterized by the presence of a 260 base pair HindIII - BamHI fragment. These plasmids were called pJR1.

EXPERIMENT 12

Construction of plasmids pDHC1 and pDHC4

A. Isolation of a 730 bp HinfI fragment from pTOM6
PTOM6 (NCIB accession No. 12351) was treated with HinfI for 2 hours at 37° C. under standard conditions. The 730 bp HinfI fragment (FIG. 3) was isolated after separation on agarose gels. The cohesive ends of this fragment were filled in with DNA polymerase Klenov fragment A. The DNA was phenol extracted and ethanol precipitated.

B. Linearization of pDH51

1 μg pDH51 was treated with SmaI for 2 hours at 37° C. under standard conditions. The reaction was stopped by phenol extraction. The linearized vector was then precipitated with ethanol, washed and resuspended in water.

C. Cloning of the pTOM6 HinfI fragment into pDH51

The isolated HinfI fragment from pTOM6 (A) and the linearized vector (B) were ligated overnight under standard conditions. The ligation mix was used to transform competent TG2 cells. The transformation mix was plated onto ampicillin-containing plates. Clones were selected, DNA isolated and analyzed by digestion with BamHI and HindIII restriction enzymes. Plasmids were identified, and were named pDHC1 and pDHC4. pDHC1 contains the HinfI fragment in the antisense orientation; pDHC4 contains the HinfI fragment in the sense orientation.

EXPERIMENT 13

Construction of plasmid pCB1

A. Isolation of a PG promoter fragment This was carried out as described in Experiment B. Insertion of a SpeI site into the PG promoter fragment.

This was carried out as described in Experiment 2B above. The resulting plasmid was called PCB1.

EXPERIMENT 14

Construction of plasmid pJR2

A. Isolation of the PG promoter fragment from pCB1
This was carried out as described in Experiment 3A.

B. Preparation of pJR1 for insertion of the PG promoter fragment.

5 μg of pJRI (constructed in Experiment 11) was cut with NcoI for 2 hours at 37° C. under standard conditions. The DNA was purified by extraction with phenol and chloroform. The cohesive ends were filled in using DNA polymerase I Klenow fragment A for 15 minutes at room temperature. The volume was increased and BamHI added. The mixture was incubated for 2 hours at 37° C. The mixture was then fractionated on agarose gels, and the large fragment of approximately 3 kb isolated by electroelution.

C. Cloning of the PG promoter into the large fragment from pJR1

PJR1 prepared as in B above was ligated with the PG promoter fragment prepared in A under standard conditions for 24 hours at 16° C. An aliquot of the ligation mixture was used to transform competent TG2 cells. Aliquots of the transformation mixture were plated onto L plates containing ampicillin and Xgal. Colonies were picked and examined for the presence of the PG promoter DNA by electrophoresis on agarose gels in order to detect an increase in the size of the vector and by direct DNA sequence determination. Plasmids containing the PG promoter were called pJR2.

CONSTRUCTION OF ANTISENSE AND SENSE pG VECTORS

A series of antisense and sense (control) vectors containing different portions of the pG cDNA and pG gene were constructed for use in regenerating transgenic plants. The vectors produced are summarized in Table 1. The vectors constructed are based on pJR1 and pJR2. DNA fragments have been inserted into these vectors both into the antisense (A) and sense (B) orientations. Expression cassettes contained in these vectors were then transferred to Bin19 (Bevan (1984) Nucleic Acids Research, 12, 8711-8721) for transformation of tomato plants.

TABLE 1

| Vectors based on | Name of antisense vector | Name of sense vector | PG fragment (see FIG. 2) |
|---|---|---|---|
| pJR1 | pJR16A | pJR16S | 740 bp HinfI |
|  | pJR36A | pJR36S | fragment a |
|  | pJR56A | pJR56S | fragment b |
|  | pJR76A | pJR76S | fragment c |
| pJR2 | pJR26A | pJR26S | 740 bp HinfI |
|  | pJR46A | pJR46S | fragment a |
|  | pJR66A | pJR66S | fragment b |
|  | pJR86A | pJR86S | fragment c |

EXAMPLE 10

Construction of PG antisense vectors pJR16A and pJR16S pJR16A

A. Isolation of a 740 bp pG antisense fragment 5 g pDHC1 was cut with KpnI and PstI at 37° C. for 2 hours under standard conditions. The 740 bp KpnI - PstI fragment was isolated after agarose gel electrophoresis by electroelution. The fragment was extracted with phenol and chloroform and ethanol precipitated. The fragment was then resuspended in 10 μl TE.

B. Preparation of pJR1

1 μg pJR1 (from Experiment 14) was cut with KpnI and PstI at 37° C. for 2 hours. The reaction was stopped by extraction with phenol and chloroform. The DNA was precipitated with ethanol, washed and dried. The vector was resuspended in 20 μl TE.

C. Ligation of the PG antisense fragment and pJR1

The products of (A) and (B) above were ligated at 16° C. for 24 hours under standard conditions. The ligation was used to transform competent TG2 cells and the mixture was plated onto ampicillin-containing plates to select transformed cells. Single colonies were grown up to prepare plasmid DNA. The DNA was analyzed for the presence of 500 bp HindIII fragment. A clone containing this fragment was identified and called pJR16A.

pJR16S

D. Isolation of a 740 bp PG sense fragment 5 μg pDHC4 was cut with KpnI and PstI at 37° C. for 2 hours under standard conditions. The 740 bp fragment produced was isolated after agarose gel electrophoresis by electroelution. The fragment was extracted with phenol and chloroform and precipitated with ethanol. The fragment was then suspended in 10 μl TE.

F. Ligation of the PG sense fragment to pJR1

The products of (D) were ligated at 16° C. for 24 hours under standard conditions. The ligation mix was used to transform competent TG2 cells and the mixture was plated onto ampicillin containing plates. Single colonies were grown up to prepare plasmid DNA. The DNA was analyzed for the presence of a 900 bp HindIII fragment. A suitable clone was identified and called pJR16S.

EXAMPLE 11

Transfer of pJR16A and pJR16S to Bin 19

A. Isolation of the 1600 bp expression cassettes pJR16A and pJR16S were cut with EcoRI at 37° C. for 2 hours under standard conditions. An aliquot of the reaction mixture was separated by agarose gel electrophoresis to check that the reaction had gone to completion. It was then heated to 65° C. for 15 minutes in order to inactivate the enzyme. The DNA was then cut partially with a small amount of HindIII in order to give all the possible EcoRI/HindIII partial digestion fragments. The EcoRI - HindIII fragment of approximately 1600 bp consisting of the 35S CaMV promoter, the PG insert sequences and Nos 3' end (expression cassette) was isolated after agarose gel electrophoresis by electroelution. The fragment was extracted with phenol and chloroform, and precipitated with ethanol. The fragment was washed, dried and resuspended in 10 μl TE.

B. Preparation of Bin19 for cloning

5 μg Bin19 DNA was cut with EcoRI and HindIII at 37° C. for 2 hours under standard conditions. The reaction was stopped by phenol and chloroform extraction, and DNA was precipitated with ethanol. The vector prepared in this fashion was resuspended in 20 μl.

C. Ligation of Bin19 to PG expression cassettes

The products of (A) and (B) were set up for ligation. Aliquots of the PG antisense and sense cassettes were ligated to Bin19 at 16° C. for 24 hours under standard conditions. The ligation mixes were used to transform competent TG2 cells which were plated on L agar containing Kanamycin and Xgal. Recombinant colonies were identified by their white color. A number of these were picked from each ligation reaction and used to prepare plasmid DNA. The DNA was analyzed for the relevant restriction pattern by cutting with EcoRI and HindIII.

EXAMPLE 12

Construction of PG antisense vectors pJR26A and pJR26S pJR26A

A. Isolation of a 740 bp PG antisense fragment

5 μg PDHC1 were cut with KpnI at 37° C. for 2 hours under standard conditions. The cohesive ends of the molecule were filled in with T4 DNA polymerase under standard conditions. The reaction was stopped by heating at 65° C. for 15 minutes. The DNA was then also cut with PstI at 37° C. for 2 hours under standard conditions. The resulting 740 bp KpnI (blunt) - PstI fragment was isolated after agarose gel electrophoresis by electroelution. The fragment was extracted with phenol and chloroform, and precipitated with ethanol. The fragment was then resuspended in 10 μl TE.

B. Preparation of pJR2

1 μg PJR2 (from Experiment 14) was cut with HincII and PstI at 37° C. for 2 hours under standard conditions. The reaction was terminated by extraction with phenol and chloroform and precipitated with ethanol. The purified vector was resuspended in 20 μl TE.

C. Ligation of PG fragments to pJR2

The products of (A) and (B) above were ligated at 16° C. for 24 hours under standard conditions. The ligation mix was used to transform competent TG2 cells. The transformation mix was plated onto ampicillin-containing plates and incubated at 37° C. overnight. Transformed colonies were grown up and plasmid DNA was prepared for analysis. A clone was identified which contained a 2 Kb EcoR1 - HindIII insert. This clone was called pJR26A.

pJR26S

D. Isolation of the 740 bp PG fragment

5 μg pDHC4 were cut with KpnI at 37° C. for 2 hours under standard conditions. The cohesive ends of the DNA were filled in with T4 DNA polymerase. The reaction was stopped by heating to 65° C. for 15 minutes. The DNA was then also cut with PstI. The resulting 740 bp fragment was isolated after agarose gel electrophoresis by electroelution. The fragment was extracted with phenol and chloroform and precipitated with ethanol. It was then resuspended in 10 μl TE.

E. Ligation of the PG sense fragment to pJR2

The products of (B) and (D) above were ligated at 16° C. for 24 hours under standard conditions. The ligation mix was used to transform competent TG2 cells, plated onto ampicillin containing plates and incubated at 37° C. overnight. Transformed single colonies were grown up and plasmid DNA was prepared. The DNA was analyzed for the presence of a 1.6 Kb EcoRI - HindIII fragment. A clone was identified and called pJR26S.

EXAMPLE 13

Transfer of pJR26A and pJR26S to Bin19

A procedure essentially the same as described above in Example 11 was used to subclone the 2.6 Kb EcoRI - HindIII partial fragments from pJR26A and pJR26S into Bin19 cut with EcoR1 and HindIII. Recombinants were identified by their white color reaction after plating onto L-agar plates containing kanamycin and Xgal. Recombinants were characterized by restriction digestion with EcoR1 and HindIII.

EXAMPLE 14

Construction of vectors pJR36A, pJR36S (fragment a) and pJR46A and pJR46S (fragment b)

A. Isolation of fragments (a) and (b)

5 μg pDHC4 (from Experiment 12) was cut with KpnI and BamHI at 37° C. for 2 hours under standard conditions. The 500 bp fragment was isolated after agarose gel electrophoresis by electroelution, extracted with phenol, chloroform and resuspended in 20 1 TE. The KpnI - BamHI fragment was then cut with HindIII. The cohesive ends of the fragment were filled with T4 DNA polymerase. The resulting fragments: a) 199 bp HindIII - KpnI (blunt ended) and b) 275 bp HindIII - BamH1 (blunt ended) were isolated after agarose gel electrophoresis by electroelution, extracted with phenol and chloroform, and resuspended in 10 1 TE.

B. Preparation of pJR1

1 μg pJR1 (from Experiment 11) was cut with SmaI at 37° C for 2 hours under standard conditions. The reaction was stopped by extraction with phenol and chloroform, and Precipitated with ethanol. The vector was then resuspended in 20 μl TE.

C. Ligation of fragment (a) into pJR1 pJR36A and pJR36S

Fragment (a) from (A) above was ligated to SmaI cut pJR1 (from (B) above) at 16° C. for 24 hours under standard conditions. The ligation mixture was used to transform competent TG2 cells which were then plated onto ampicillin-containing plates. Transformed colonies were grown up and used for plasmid DNA preparation. EcoRI/PstI double digests identified those clones containing fragment (a) inserts. The EcoRI - PstI inserts of these clones were isolated and subcloned into M13 mp8 which had been cut with EcoRI and PstI. DNA sequence analysis was carried out in order to ascertain the orientation of the insert (a). Clones obtained from this experiment were called pJR36A and pJR36S, according to the orientation of the insert.

D. Ligation of fragment (b) into pJR1
PJR56A and pJR56S

Fragment (b) from (A) above was ligated to SmaI cut pJR1, from (B) above, at 16° C. for 24 hours under standard conditions. The ligation mixture was used to transform competent TG2 cells which were then plated onto ampicillin containing plates. Transformed colonies were grown up and used for plasmid DNA preparation. EcoR1/PSEI double digests identified those clones containing fragment (b) inserts. The EcoR1 - pstI inserts of these clones were isolated and subcloned into M13 mp8 which had been cut with EcoRI and PstI. DNA sequence analysis was carried out in order to ascertain the orientation of the insert (b). Clones obtained from this experiment were called pJR56A and PJR56S, according to the orientation of the insert.

EXAMPLE 15

Transfer of pJR36A/S and pJR56A/S to Bin19

A. Preparation of expression cassettes containing fragments (a) and (b) in pJR1

5 µg each of pJR36A, pJR36S, pJR56A and pJR56S were cut separately with EcoRI and HindIII at 37° C. for 2 hours under standard conditions. The resulting four fragments containing (a) 930 bp and (b) 1000 bp were isolated separately after electrophoresis on agarose gels by electroelution. The fragments were extracted with phenol and chloroform, and precipitated with ethanol. The four fragments were then resuspended in 10 µl TE.

B. Preparation of Bin19

Bin19 was cut with EcoRI and HindIII for 2 hours at 37° C. under standard conditions. The reaction was stopped by addition of phenol and chloroform. After extraction the DNA was precipitated with ethanol, and resuspended in 20 µl TE.

C. Ligation of the fragments to Bin19

The four EcoRI - HindIII fragments isolated in A were set up for separate ligation reactions using Bin19 prepared as described in B under standard conditions. The ligation mixtures were used to transform competent TG2 cells which were plated onto L agar containing kanamycin and Xgal. After incubation overnight, recombinant colonies were identified by their white color. A number of the clones were picked from each separate ligation and were used to prepare DNA. The DNA's were analyzed for the presence of a EcoRI - HindIII fragment of the appropriate size for the insertion of the expression cassettes to Bin19.

EXAMPLE 16

Construction of pJR46A, pJR46S (fragment a) and pJR66A, pJR66S (fragment b)

A. Preparation of pJR2

1 µg pJR2 (from Experiment 14) was cut with HincII at 37° C. for 2 hours under standard conditions. The reaction was terminated by extraction with phenol and chloroform. The vector was precipitated with ethanol, washed and resuspended in 20 µl TE.

pJR46A and pJR46S

B. Ligation of PG fragment (a) to pJR2

Fragment (a) from Example 14(A) above was ligated to HincII cut pJR2 from (A) above at 16° C. for 24 hours under standard conditions. The ligation mixture was used to transform competent TG2 cells which were then plated onto ampicillin containing plates. Transformants were picked, grown up and used to prepare plasmid DNA. Plasmid DNA was cut with both EcoRI and PstI. DNA from clones which contained inserts were restricted with EcoRI and PstI. The EcoRI - PstI inserts were isolated after agarose gel electrophoresis by electroelution and subcloned into M13mp8 which had been cut with EcoRI and PstI. DNA sequence analysis was used to ascertain the orientation of the inserts (a). Clones were obtained from this experiment were called pJR46A and pJR46S, according to the orientation of the insert.

pJR66A and pJR66S

Fragment (b) from Example 14(A) was ligated to HincII cut, from A above, separately at 16° C. for 24 hours under standard conditions. The ligation mixture was used to transform competent TG2 cells which were then plated onto ampicillin containing plates. Transformants were picked, grown up and used to prepare plasmid DNA. Plasmid DNA was cut with both EcoRI and PstI. DNA from clones which contained inserts were restricted with EcoRI and PstI. The EcoRI - PstI inserts were isolated after agarose gel electrophoresis by electroelution and subcloned into M13 mp8 which had been cut with EcoRI and PstI. DNA sequence analysis was used to ascertain the orientation of the inserts (b). Clones were obtained from this experiment were called pJR66A and pJR66S, according to the orientation of the insert.

EXAMPLE 17

Transfer of pJR46A, pJR46S, pJR66A and pJR66S to Bin19

A. Preparation of expression cassettes containing fragments (a) and (b) in pJR2

5 g of each of pJR46A, pJR46S, pJR66A and pJR66S were cut separately with EcoRI and HindIII at 37° C. for 2 hours under standard conditions. The resulting four fragments of approximately 2.5 kb were isolated separately after gel electrophoresis by electroelution. The fragments were extracted with Phenol and chloroform, and precipitated with ethanol. The four fragments were then resuspended in 10 µl TE.

B. Ligation of expression cassettes into Bin19

Aliquots containing the four fragments from (A) were ligated to Bin19 DNA prepared as described in Example 15 (B) in separate ligation reactions under standard conditions. The ligation mixtures were used to transform competent TG2 cells. The transformation mixture was plated onto L-agar plates containing kanamycin and Xgal. After overnight incubation recombinant colonies were identified by their white color. A number of clones for the separate experiments were picked and DNA was prepared. The DNAs were analyzed for the presence of the appropriate EcoRI - HindIII fragments.

EXAMPLE 18

Construction of PG vectors pJR76A and pJR76S

A. Isolation of fragment (c)

10 μg gTOM 23 (a genomic clone containing the PG gene, NCIB No 12373) was cut with HindIII and BamHI. The 1.98 Kb fragment was isolated after agarose gel electrophoresis by electroelution. The cohesive ends of the fragment were filled in with T. DNA polymerase.

B. Ligation of fragment (c) to pJR1

The products from (A) above and Example 14 (B) (ie. pJR1 cut with SmaI) were ligated at 16° C. for 24 hours under standard conditions and the mixture used to transform competent TG2 cells which were then plated onto plates containing ampicillin. Transformed colonies were grown up and used to prepare plasmid DNA. The DNA was cut with EcoRI and the orientation of the insert determined from the pattern of fragments obtained. The clones were called pJR76A and PJR76S according to the orientation of the insert.

EXAMPLE 19

Transfer of vectors pJR76A and pJR76S to Bin19

A. Preparation of expression cassettes from pJR76A and pJR76S

5 μg of each clone was cut with HindIII at 37° C. for 2 hours under standard conditions. The enzyme was inactivated by heating the reaction mixture to 70° C. for 15 minutes. EcoRI was then added in concentration necessary to give partial restriction. The reactions were stopped by the addition of phenol and chloroform. The required 2.71 Kb EcoRI - HindIII fragments were isolated after agarose gel electrophoresis by electroelution. The fragments were extracted with phenol and chloroform and precipitated with ethanol. The fragments were then resuspended in 10 μl TE.

B. Ligation of the expression cassettes to Bin19

The two fragments from vectors pJR76A and pJR76S prepared in (A) were ligated separately to Bin19 (prepared as described in Example 11 B). The ligation mixture was used to transform competent TG2 cells. The transformation mix was plated onto L plates containing kanamycin and Xgal. Recombinant plasmids were identified by their white color. DNA was prepared from a number of these and analyzed for the presence of the required EcoR1 - HindIII fragments.

EXAMPLE 20

Construction of PG vectors pJR86A and pJR86S

A. Ligation of PG fragment (c) to pJR2

The products of Example 18 (A) fragment (c) and Example 16 (A) (i.e. pJR2 cut with HincII) were ligated at 16° C. for 24 hours under standard conditions and the mixture used to transform competent TG2 cells which were then plated on plates containing ampicillin. Transformed colonies were grown up and used to prepare plasmid DNA. The orientation of the insert was deduced using the EcoR1 restriction pattern. These clones were called pJR86A and pJR86S, according to the orientation of the insert.

EXAMPLE 21

Transfer of vectors pJR86A and pJR86S into Bin19

This Example was carried out essentially as described in Example 19, i.e. the vectors were cut with HindIII under conditions of partial restriction, which was then followed by restriction with EcoR1. The resulting 3.63 Kb fragment was isolated and cloned into Bin19.

All constructs in Bin19 were intended for use in separate triparental mating experiments to allow transfer to Agrobacterium, and from there to tomato plants.

INHIBITION OF PECTIN ESTERASE

In addition to polygalacturonase, pectin esterase (PE) has been implicated in softening of the tomato fruit. A ripe tomato fruit cDNA library was screened with mixed oligonucleotide probes designed from the published amino acid sequence of PE. One clone, pPE1, (NCIB Accession No. 12568) has been isolated and characterized. FIG. 3 shows the complete sequence of this cDNA clone. The deduced amino acid sequence of PE is substantially different from the sequence published by Markovic and Jornvall. 40 amino acid differences are found in the sequence of the mature PE protein; major rearrangements in the continuity of the published amino acid sequence are evident and an additional 11 amino acids are found in the protein presented here. In addition to the sequences of the mature PE, both N-terminal and C-terminal amino acid extensions are detected in the polypeptide encoded by pPE1.

We have used fragments of the cDNA to construct antisense and sense vectors. These are summarized in Table 2.

TABLE 2

| Vectors based on | Name of antisense vector | Name of sense vector | Fragment |
|---|---|---|---|
| pJR1 | pJR101A | pJR101S | 420 bp PstI |
|  | pJR111A | pJR111S | 351 bp BbvI |
| pJR2 | pJR102A | pJR102S | 420 bp PstI |
|  | pJR112A | pJR112S | 351 bp BbvI |

CONSTRUCTION OF ANTISENSE PE VECTORS

EXAMPLE 30

Preparation of pJR101A and pJR101S

A. Isolation of a 420 bp fragment from pPE1

Plasmid pPE1 was cut with PstI at 37° C. for 2 hours under standard conditions. The 420 bp PstI fragment was isolated after agarose gel electrophoresis by electroelution, extracted with phenol and chloroform and precipitated with ethanol. The DNA was then resuspended in 10 μl TE.

B. Preparation of pJR1 pJR1 (from Experiment 11) was cut with PstI at 37° C. for 2 hours under standard conditions. The reaction was stopped by the addition of phenol, precipitated with ethanol and resuspended in 20 μl TE.

C. Ligation of PE fragment to pJR1

The products of steps (A) and (B) above were ligated under standard conditions and the ligation mixture was used to transform competent TG2 cells. The transformation mix was subsequently plated onto ampicillin containing plates and incubated at 37° C. overnight. Transformed colonies were grown up and used to prepare plasmid DNA. Clones were identified which gave 420 bp fragment on digestion with PstI. The 650 bp BamHI - HindIII fragments from these clones were isolated after agarose gele electrophoresis by electroelution and cloned into M13mp8. The orientation of the PstI insert was determined by sequence analysis. Clones identified were named pJR101A and pJR101S according to the orientation of the insert.

EXAMPLE 31

A. Isolation of a 1.2 Kb EcoR1 - HindIII fragment

Plasmids pJR101A and pJR101S were cut separately with EcoR1 and HindIII at 37° C. for 2 hours under standard conditions. The resulting 1.2 Kb fragments were isolated after gel electrophoresis from agarose gels by electroelution. The DNA was then extracted with phenol and chloroform, precipitated with ethanol, and resuspended in 20 µl TE.

B. Preparation of Bin19

Bin19 was cut with EcoR1 and HindIII for 2 hours at 37° C. under standard conditions. The enzymes were removed by phenol extraction and the vector precipitated with ethanol. The DNA was then resuspended in water.

C. Ligation of the PE expression cassette to Bin19

Aliquots of the products of reactions A and B were ligated for 16 hours at 16° C. under standard conditions. The ligation mix was used to transform competent TG2 cells. The transformation mix was plated onto plates containing kanamycin. DNA was picked from individual clones and analyzed for the presence of the 1.2 Kb EcoR1 - HindIII fragment.

EXAMPLE 32

Construction of vectors pJR102A and pJR102S

The construction of these vectors followed the construction of pJR101A and pJR101S (Example 30), except that the 420 bp PstI PE fragment was inserted into pJR2 (from Experiment 14).

EXAMPLE 33

Transfer of vectors pJR102A and pJR102S to Bin19

Transfer of the PE expression cassettes Bin 19 was carried out as described in Example 31 for the transfer of pJR102A and pJR102S into Bin19.

EXAMPLE 34

Construction of vectors pJR111A and pJR111S

A. Isolation of a 351 bp fragment from pPE1

Plasmid pPE1 was cut with BbvI at 37° C. for 2 hours under standard conditions and the cohesive ends filled using T4 polymerase. The 351 bp fragment was isolated after agarose gel electrophoresis by electroelution, extracted with phenol and chloroform and precipitated with ethanol. It was then resuspended in 10 µl TE.

B. Preparation of PJR1

1 µg pJR1 (from Experiment 11) was cut with SmaI for 2 hours at 37° C. under standard conditions. The reaction was terminated by the addition of phenol and chloroform. After extraction the DNA was precipitated with ethanol, and resuspended in 10 µl TE.

C. Ligation of the PE fragment to pJR1

The products of (A) and (B) were ligated at 16° C. for 24 hours under standard conditions. The ligation mix was used to transform competent E.coli TG2 cells. The transformation mix was plated onto ampicillin-containing Plates. Single colonies were grown up and analyzed for the presence of a 900 bp EcoR1 - PstI fragment. This fragment was isolated by electroelution after agarose gel electrophoresis and cloned into M13 mp8 (commercially available vector). The orientation of the fragment was determined by DNA sequence analysis.

EXAMPLE 35

Transfer of vectors pJR111A and pJR111S to Bin 19

A. Isolation of the 1.1 Kb EcoR1 - HindIII fragment

Plamids pJR111A and pJR111S were cut with EcoR1 and HindIII at 37° C. for 2 hours under standard conditions. The 1.1 Kb fragment was isolated after agarose gel electrophoresis by electroelution. It was extracted with phenol and chloroform, precipitated with ethanol and resuspended in 20 µl TE.

B. Ligation of the PE expression cassettes into Bin19.

Aliquots of the products of (A) and Example 31 (B) were ligated at 16° C. for 24 hours. The ligation mixtures were used to transform competent E.coli TG2 cells. The transformation mix was plated onto plates containing kanamycin. Single colonies were used for DNA extraction and clones identified by the presence of the 1.1 Kb EcoR1 - HindIII fragment.

EXAMPLE 36

Construction of vectors pJR112A and pJR112S

Construction of these vectors followed the procedure in Example 34 for the construction of vectors pJR111A and pJR111S except that the 351 bp BbvI fragment was inserted into pJR2 from Experiment 14, rather than pJR1.

EXAMPLE 37

Transfer of vectors pJR112A and pJR112S to Bin19

Transfer of the PE expression cassettes from pJR112A and pJR112S into Bin19 followed the protocol described in example 35.

EXAMPLE 40

Transformation of Tomato Stem Explants

A. Transfer of Bin19 vectors to Agrobacterium

The recombinant vectors prepared in Example 11 were mobilized from E.coli (TG-2) to Agrobacterium tumefaciens (LBA4404) (Hoekma A, Hirsch PR,Hooykaas PJJ and Schilperoort RA, 1983, Nature 303 pp 179–180) in a triparental mating on L-plates with E.coli (HB101) harboring pRK2013 (Ditta G. et al, 1980 PNAS, USA, Vol 77, pp7347–7351) Transconjugants were selected on minimal medium containing kanamycin (50µg/cm$^3$) and streptomycin (500 µg/cm$^3$).

B. Preparation of Agrobacteria for transformation

L-Broth (5cm$^3$) containing kanamycin at 50 µg/cm$^3$ was inoculated with a single bacterial colony. The culture was grown overnight at 30° C. with shaking at 150 r.p.m. This culture (500 µ) was inoculated into L-Broth containing kanamycin (50 µg/cm$^3$) and grown as before. Immediately before use the Agrobacteria were pelleted by spinning at 3000 r.p.m. for 5 minutes and resuspended in an equal volume of liquid Murashige and Skoog (MS) medium.

C. Preparation of plant tissue for transformation

Feeder plates were prepared in 9 cm diameter petri dishes as follows. Solid MS medium supplemented with 5 uM zeatin riboside and 3 uM IAA aspartic acid was overlaid with Nicotiana tabacum var Samsun suspension culture (1cm$^3$). One 9 cm and one 7 cm filter paper discs were placed on the surface. Hypocotyls from 4 week old seedlings grown on MS medium were excised and placed on feeder plates. The plates were sealed with Nescofilm and incubated overnight in the plant growth room (26° C. under bright fluorescent light).

D. Transformation Protocol

Hypocotyls from the feeder plates were placed in the Agrobacteria suspension in 12 cm diameter petri dishes and cut into approximately 1 cm lengths, removing all leaf and cotelydon axes. After 20 minutes the hypocotyl segments were returned to the feeder plates which were sealed and replaced in the growth room. After 48 hours incubation in the growth room the plant material was transferred to MS medium supplemented with 5 μM zeatin riboside, 3 μM IAA aspartic acid, 500 μg/cm$^3$ carbenicillin and 50 μg/cm$^3$ kanamycin in petri dishes. The petri dishes were sealed and returned to the growth room.

From six weeks after inoculation with Agrobacterium, shoots were removed from the explants and placed on MS medium supplemented with carbenicillin (200 μg/cm$^3$) for rooting.

Transformed plants rooted 1-2 weeks after transfer. These plants were then grown in tissue culture for a number of weeks before being transferred to pots. These plants were then grown in growth rooms or greenhouses as appropriate.

EXPERIMENT 40

Analysis of Transformed Plants Produced in Example 40

A. Analysis of leaves for the production of antisense RNA

RNA was extracted from leaves following published procedures. RNA was probed for the presence of antisense RNA by dot hybridization using either sense or antisense specific probes. The results were considered to demonstrate the presence of antisense RNA in leaves from plants containing antisense constructs.

B. Southern analysis Of transformed plants

DNA was extracted from leaves of transformed plants. DNA was cut with various restriction enzymes, separated on agarose gels and transferred to nylon membranes. DNA was probed with appropriate labelled DNA fragments for the presence of the antisense and sense constructs. At the time of writing results are not to hand but a Southern blot has been obtained indicating that DNA from the construct JR16A has been incorporated into the genome of a tomato plant.

C. Analysis of antisense RNA production in tomato fruit

It is currently intended to extract RNA at different stages of ripening from transformed tomato fruit following published procedures. RNA will be probed with specific DNA probes for the production of antisense RNA.

D. Effect of antisense RNA production of fruit softening

Experiments are also planned to demonstrate how the presence of antisense RNA affects the process of fruit ripening.

What is claimed is:

1. Recombinant DNA comprising:
   an upstream promoter base sequence,
   a base sequence for transcription into mRNA under control of said upstream promoter base sequence comprising coding and template strands, and
   a downstream transcription terminator base sequence,
   wherein the coding strand of said base sequence for transcription comprises an inverted sequence of bases complementary to a run of bases of pectin esterase mRNA, wherein the transcript of said base sequence for transcription substantially inhibits expression of tomato pectin esterase.

2. The recombinant DNA according to claim 1, wherein said base sequence for transcription comprises a sequence of bases complementary to a part of the sequence set forth in FIG. 3.

3. The recombinant DNA according to claim 1, wherein said upstream promoter sequence is a constitutive promoter.

4. The recombinant DNA according to claim 3, wherein said constitutive promoter is the CaMV 35S promoter.

5. The recombinant DNA according to claim 1, wherein said upstream promoter sequence is the polygalacturonase promoter.

6. A vector comprising said recombinant DNA according to claim 1.

7. A plant cell comprising said recombinant DNA according to claim 1.

8. A dicotyledonous plant comprising said cell according to claim 7.

9. The plant according to claim 8, wherein said plant is a tomato plant.

* * * * *